United States Patent [19]

Schubert et al.

[11] 4,112,006
[45] Sep. 5, 1978

[54] PROCESS FOR NITRATING TOLUENE

[75] Inventors: Hans Schubert, Kelkheim; Friedrich Wunder, Flörsheim, Main, both of Fed. Rep. of Germany

[73] Assignee: Hoechst Aktiengesellschaft, Frankfurt am Main, Fed. Rep. of Germany

[21] Appl. No.: 816,213

[22] Filed: Jul. 15, 1977

[30] Foreign Application Priority Data

Jul. 17, 1976 [DE] Fed. Rep. of Germany ....... 2632234

[51] Int. Cl.² .............................................. C07C 79/10
[52] U.S. Cl. .................................... 260/645; 260/688
[58] Field of Search ......................................... 260/645

[56] References Cited

U.S. PATENT DOCUMENTS

| 2,431,585 | 11/1947 | Rout ..................................... 260/645 |
| 3,957,889 | 5/1976 | Milligan et al. ...................... 260/645 |
| 3,965,200 | 6/1976 | Manabe et al. ...................... 260/645 |

OTHER PUBLICATIONS

Topchiev, Nitration of Hydrocarbons and Other Organic Compounds, Pergamon Press, New York, 1959, pp. 278, 279 and 282.

Primary Examiner—Leland A. Sebastian
Attorney, Agent, or Firm—Curtis, Morris & Safford

[57] ABSTRACT

Toluene is nitrated with nitric acid in the gaseous phase under reduced pressure and at temperatures from about 80° – 180° C, while using an acidic inorganic catalyst consisting of a carrier substance based on $SiO_2$ and/or $Al_2O_3$ impregnated with a high boiling inorganic acid such as $H_2SO_4$ or $H_3PO_4$ and optionally with metal salts of such acids. This process yields essentially p-nitrotoluene, in addition to a smaller quantity of o-nitrotoluene and a very small amount of m-isomer. The technology of the process is simple and provides good yields. The nitrotoluenes, especially the p,nitrotoluene are interesting intermediates, for example for the manufacture of dyestuffs.

5 Claims, No Drawings

PROCESS FOR NITRATING TOLUENE

The present invention relates to a process for nitrating toluene in the gaseous phase under reduced pressure and at an elevated temperature in the presence of catalysts, yielding a nitrotoluene mixture containing essentially p-nitrotoluene.

Nitrotoluenes are important intermediates, for example for the manufacture of dyestuffs, p-nitrotoluene being in general the most important isomer.

Nitration is widely used on a technical scale. Several methods for carrying out this nitration are known. The usual method of operating which uses a mixture of sulfuric acid/nitric acid (= "nitrating acid;" cf. for example Winnacker-Kuchler, "Chemische Technologie," vol. 3, pg. 828 (1959) and Houben-Weyl, "Methoden der Organischen Chemie," vol. 10/1, pg. 515–518 (1971)) exhibits a ratio of p-nitrotoluene to o-nitrotoluene in the nitration product of e.g. about 0.63. The nitration product contains additionally about 1–2% of m-nitrotoluene. Since the conventional nitrating method which uses nitrating acid leads to the formation of only about 33% of p-isomers, it is unsuitable, if the main interest focuses on the manufacture of p-isomer.

Some prior research work has been done which has resulted in the nitration of toluene having a higher concentration of the p-component in the nitration product. As described, for example, in "Chemistry Letters," pg. 33–34 (1972) or in "Nippon Kagaku Kaishi," issue 1, pg. 122–126 (1974), the nitration of toluene with highly concentrated nitric acid in the liquid phase under normal pressure and at elevated temperature, while using porous material such as Celite 545 (a trade name for a kieselguhr) on which are applied aromatic sulfonic acids such as toluene-2,4-disulfonic acid, m-benzene disulfonic acid or o-, m-, p-nitrobenzene sulfonic acids, is directed in such a way that a toluene nitration product is formed having an isomer ratio of p-nitrotoluene to o-nitrotoluene of 1.6.

However, in spite of this surprisingly good isomer ratio, this method suffers nevertheless from serious disadvantages, for said isomer ratio of at a maximum 1.6 can be reached only by using a large excess of toluene, calculated on the quantity of $HNO_3$ employed, by using moreover a relatively large quantity of catalyst and by nitrating exclusively with highly concentrated $HNO_3$.

Also this nitrating method cannot be practiced on an industrial scale, since a large-scale nitration does not permit binding of the water of reaction formed by application of the sulfonic acids onto the carrier, so that the sulfonic acids used in the catalyst for the nitrating process and the highly concentrated $HNO_3$ which is added dropwise are excessively diluted with water and therefore the catalyst rapidly loses its directing activity.

Therefore, there was a need for solving the problem of how to modify the known toluene nitration process in such a way as to provide an acceptable technical operation without diminishing the proportion of p-isomers in the reaction product. The present invention solved this problem in an excellent and simple manner.

The present invention consists of a process for so nitrating toluene that, the main product is p-nitrotoluene, by reacting toluene with nitric acid in the presence of an inorganic catalyst that is impregnated with an acid component; the process comprises carrying out the reaction in the gaseous phase under reduced pressure, especially under a pressure of from about 1 to 100 mm Hg, or even better from about 20 to 50 mm Hg, and at a temperature of from about 80° to 180° C., preferably from about 100° to 140° C., in the presence of a carrier substance based on $SiO_2$ and/or $Al_2O_3$ that is impregnated with a high boiling inorganic acid and optionally with metal salts of such an acid.

The carrier based on $SiO_2$ and/or $Al_2O_3$ can be practically any commercially available $SiO_2$ or $Al_2O_3$ aluminosilicate preparation, and may additionally contain minor quantities of different inorganic oxides such as MgO etc. For impregnating this carrier substance there are used high boiling inorganic acids such as $H_3PO_4$, $H_2SO_4$ etc. The addition of metal salts, especially of heavy metal salts, to such acids is useful for carrying out this impregnation. Especially good results are obtained, when the carrier substance is impregnated with $H_2SO_4$ and a sulfate with a trivalent metal cation, especially with $Fe_2(SO_4)_3$ and/or $Al_2(SO_4)_3$. These catalysts are prepared in a simple manner by blending the carrier substance with the aqueous solutions of the acid and salt components and by calcining the thus treated catalysts prior to their use, at about 100°–200° C., preferably at 100°–120° C. The impregnating agents, i.e. the high boiling inorganic acids and optionally the corresponding metal salts, should be applied in an amount of about 1–40, preferably about 5–20% by weight of the carrier substance.

The carrier substances may be used in various forms. However, preference is given to balls having a diameter of about 3–6 mm. The inorganic catalysts impregnated with an acid component and used for the process of the present invention are already known in principle as catalyst substances for nitrating unsubstituted and halogenated aromatic hydrocarbons such as benzene, chlorobenzene, dichlorobenzene, o-chlorotoluene etc. in the vapor phase under normal pressure while using $HNO_3$ or $NO_2$ (cf. British Pat. No. 586,732, Russian Pat. No. 380,639, CA 79, 52984z, German Offenlegungsschrift No. 2,408,664 and German Offenlegungsschrift 2,510,095). However there was no reason to expect that the nitration in the gaseous phase could also be performed satisfactorily on benzene derivatives that are substituted in the nucleus only by one or more alkyl radicals, and not also by groups that reduce the density of electrons in the nucleus such as Cl, since the nitration of such alkyl-substituted benzenes would be expected to result in oxidation or resinification. This is especially true since, for example, toluene (cf. Ullmanns Encyclopadie der technischen Chemie 8, 369 (1974) and Kirk-Othmer "Encyclopedia of Chemical Technology" 3, 421 (1964)) is easily converted to benzoic acid at temperatures above 150° C. with diluted 10–15% $HNO_3$ and under a pressure from 10–70 bars, and to nitrobenzoic acids under the influence of concentrated nitric acid. Moreover, p-nitrotoluene is oxidized at 195° C. with diluted 25%-nitric acid (cf. Houben-Weyl "Methoden der organischen Chemie" 8, 386–387 (1952)) without difficulty to yield p-nitrobenzoic acid, and o-xylene, m-xylene or p-xylene (cf. the same literature as stated above) to yield the corresponding toluyl acids or dicarboxylic acids with the use of nitric acid of various concentrations and at suitable temperatures and pressures.

Surprisingly it has been found according to the present invention, that toluene may be nitrated to yield a nitration mixture with an extremely high portion of p-isomer, if the above-mentioned catalysts are used in the gaseous phase with nitric acid, under reduced pressure and at elevated temperature. The isomer ratio of p-nitrotoluene to o-nitrotoluene is consistently within the range from 1.4–2.0.

As far as the method of nitration of toluene in the gaseous phase according to the invention is concerned, the most important factor is the carrying out of the reaction in vacuo, for careful research work proved that an isomer ratio p/o of 1.4 to 2.0 that was achieved at high vacuum, diminished constantly in favor of o-isomers with increasing pressure and that the isomer ratio fell to only about 0.8 to 1.00 under normal pressure. Hence, the largest isomer shift towards the p-component occurs at high vacuum. The practice showed, however, that a vacuum between 20 and 50 mm Hg is fully sufficient, because a further reduction of the pressure brings about only insignificant shifts of the isomers towards p-nitrotoluene.

When comparing this nitration in the gaseous phase with those gaseous phase nitrations mentioned above, the method according to the invention exhibits the further advantage that the established vacuum permits operation at relatively low temperatures, i.e. about 80° C. to 180° C., preferably at 100° to 140° C. An additional advantage resides in the fact that the nitration of toluene may be carried out under milder conditions at these relatively low temperatures; for, as shown by parallel experiments under normal pressure or in vacuo, a nitration at temperatures from about 230° C. to 250° C. produced strong oxidation effects and diminished the yield. The low temperature of the method according to the invention also favors essentially the isomer shift; actually, at temperatures above 200° C., the isomer shift diminished remarkably to the detriment of the desired p-component.

As nitrating agent there may be used highly concentrated and diluted nitric acid as well nitric acid containing preferably 67 to 40% of water.

The toluene to be nitrated is used in excess and may vary from 10 to 1 mole of toluene per 1 mole of nitric acid, preferably from 3 to 1 mole of toluene per 1 mole of nitric acid.

The reactor residence times are very short and may vary from fractions of seconds to some seconds, preferably from 0.1 to 1 second.

The nitration in the gaseous phase according to the invention is carried out in such a way that the reactor charged with the above-mentioned catalyst is heated to a constant temperature of about 100° C. to 110° C., that the toluene to be nitrated or the nitric acid to be used for the nitration are evaporated separately, heated up to the catalyst temperature and blended immediately prior to contacting the catalyst. A preferred reactor is a fixed bed reactor, but a moving bed reactor or a fluidized bed reactor are also suitable with corresponding carrier materials.

The reaction mixture which is conducted over the catalyst is condensed in a subsequent cooler, whereupon the condensate separates into an organic phase (yellow) and an aqueous phase (colorless) containing non-reacted nitric acid. The organic phase is washed with diluted soda solution until no more acid is present. The isomer distribution is determined by gas chromatographic analysis and the yield worked out.

The present invention permits the nitration of toluene by very simple processing methods in such a way that the isomer ratio $p/o = 0.63$ that is reached by conventional nitrating methods with mixed acid is increased to a maximum of about 2.0. The process of the invention is highly interesting from a technological standpoint due to the simple practical processing method and due to the excellent shift of the isomer ratio towards p-nitrotoluene.

The particular advantage of the process according to the present invention resides in the fact that it produces the desired p-isomer at a high conversion and at a favorable ratio, neither the reaction water formed upon nitration nor the water entrained when using $HNO_3$ of a low concentration detrimentally affect the isomer ratio or the yield. Also the advantageous isomer ratio and the yield are not detrimentally affected by using a slight excess of toluene, calculated on the initial quantity of nitric acid.

The following examples illustrate the invention. The parts mentioned in these examples are parts by weight.

EXAMPLE 1

1200 parts of $SiO_2$ having 120 $m^2/g$ of BET (BET = a method for the determination of the surface of solids, measured in $m^2/g$ and named after its inventors Brunauer, Emmet and Teller; cf. table 6: carriers) are impregnated with a solution of 600 parts of 52% $H_2PO_4$ in 360 ml of water and dried in vacuo at 100° C. under a pressure of 200 mm Hg.

A reaction tube of duran glass is charged with 400 ml of this catalyst and after establishing a vacuum of 20 mm Hg the reaction tube is heated by electrical heating means so that the temperature in the reaction area is about 200° C. during nitration. The components toluene and 96% nitric acid are metered in separately into an evaporator under a vacuum of 20 mm Hg. They are then heated to the temperature of the catalyst and in their gaseous state conducted to the catalyst in such a way that the components are blended immediately prior to their contact with the catalyst. By this method 156 parts of toluene and 32.8 parts of 96% nitric acid ($d_{20}$ = 1.497; molar ratio of toluene : $HNO_3$ = 3:1) in their gaseous state are conducted to the catalyst per hour.

The gaseous reaction mixture is condensed upon leaving the reactor, the organic phase is separated, washed to neutrality with 5% soda solution and the proportion of isomers determined by gas chromatographic analysis. There are obtained 59.3% of the theoretical yield of mononitrotolulene, calculated on the starting quantity of $HNO_3$, the isomer distribution being $p/o = 1.23$. The nitrotoluene mixture contains about 3% of m-nitrotoluene. No dinitrotoluenes could be detected.

This processing method has been used in all examples which follow:

EXAMPLES 2 to 5

In Examples 2 through 5 nitration in the gaseous phase was carried out with the same catalyst (starting quantity of the catalyst being about 253 g — about 400 ml) while constantly using 156 parts of toluene and 32.8 parts of 96% $HNO_3$ per hour in analogy to Example 1, but with increasing pressure and increasing temperature.

Table 1

Nitration of toluene in the gaseous phase under increasing pressure and at increasing temperature, but otherwise under constant conditions.

Table 1

| No. | reaction-temperature °C | vacuum mm Hg | catalyst | yield calcul. on $HNO_3$ % | isomer distribution p/o | p : o |
|---|---|---|---|---|---|---|
| 2 | 200 | 40 | 20 % $H_3PO_4/SiO_2$ | 54.7 | 1.19 | 54.3 : 45.7 |
| 3 | 220 | 100 | 20 % $H_3PO_4/SiO_2$ | 39.9 | 1.14 | 53.3 : 46.7 |
| 4 | 225 | 150 | 20 % $H_3PO_4/SiO_2$ | 35.6 | 1.10 | 52.4 : 47.6 |
| 5 | 270 | 760 | 20 % $H_3PO_4/SiO_2$ | 27.4 | 0.88 | 46.8 : 53.2 |

EXAMPLE 6

1000 parts of $SiO_2$ as in Example 1 (cf. table 6: carriers) are impregnated with a solution of 11.4 parts of 98% sulfuric acid in 703 parts of water and dried under normal pressure at 105° C.

There are used 213 parts (about 400 ml) of this catalyst and the reaction is carried out at 140°–145° C. in vacuo under a pressure of 5 mm Hg by introducing separately 208 parts of gaseous toluene and 32.8 parts of gaseous 96% nitric acid (molar ratio of toluene to nitric acid = 2.26 : 0.5) into the reactor. Nitrotoluene is obtained with a yield rate of 68.3% of the theoretical yield, calculated on the starting quantity of $HNO_3$, this yield consisting of 38.8% of o-nitrotoluene and 4.0% of m-nitrotoluene and 57.2% of p-nitrotoluene. The isomer ratio of p/o is 1.47 and represents an isomer distribution of 59.5% of p-nitrotoluene and 40.5% of o-nitrotoluene.

EXAMPLE 7

After having charged the reactor with 231 parts (about 400 ml) of catalyst, prepared according to Example 6 of 1000 g of $SiO_2$ as per Example 1 (cf. table 6: carriers) and of a solution of 54 parts of 98% sulfuric acid in 678 parts of water, the nitration in vacuo under 20 mm Hg at 145°–150° C. is carried out in such a way that 156 parts of toluene and 32.8 parts of 96% nitric acid — both in their gaseous state — are conducted over the catalyst per hour. $HNO_3$ is converted at the rate of 51.4% and the isomer distribution is 57.5% of p-nitrotoluene and 42.5% of o-nitrotoluene (p/o = 135). The nitrotoluene mixture contains about 3.4% of m-nitrotoluene.

EXAMPLES 8 through 15

The catalysts being used for carrying out the examples 8 to 15 are prepared as follows:

a. 10% sulfuric acid on aluminosilicate 647 parts of diluted sulfuric acid, prepared from 159 parts of 98% sulfuric acid and 488 parts of water, are applied onto 1400 parts of aluminosilicate with 13% of $Al_2O_3$ (cf. table 6 : carriers) and dried at 105° C. under normal pressure.

b. 20% sulfuric acid on aluminosilicate

In analogy, 1400 parts of aluminosilicate according to a) are impregnated with a mixture of 360 parts of 98% sulfuric acid and 376 parts of water, then dried as described.

c. 10% sulfuric acid and 1% of Mo on aluminosilicate

In the same manner there is applied onto 1400 parts of aluminosilicate as in a) a solution of 28.6 parts of ammoniumheptamolybdate in 373 parts of water, being blended with 161 parts of 98% sulfuric acid, then dried at 105° C. as above described.

When using 400 ml of catalyst, under the conditions stated for the nitration of toluene in the gaseous phase, there are obtained the following isomer distributions. The yields of mononitrotoluene obtained per hour of reaction time are also specified, calculated on the starting quantity of nitric acid.

Table 2

Nitrating toluene in the gaseous phase when using alumosilicate as carrier, impregnated with sulfuric acid or a mixture of sulfuric acid/Mo.

Table 2

| No. | $CH_3$-C$_6$H$_5$ g | 96 % $HNO_3$ g | Temp. °C | Vacuum mm Hg | catalyst | yield calculated on $HNO_3$ % | Isomer ratio p/o | p : o |
|---|---|---|---|---|---|---|---|---|
| 8 | 156 | 32.8 | 150–155 | 5 | * | 66.7 | 1.49 | 59.8 : 40.2 |
| 9 | 208 | 32.8 | 150–155 | 5 | * | 71.4 | 1.39 | 58.2 : 41.8 |
| 10 | 156 | 32.8 | 140–145 | 5 | ** | 65.4 | 1.31 | 56.7 : 43.3 |
| 11 | 156 | 32.8 | 140–145 | 20 | ** | 59.4 | 1.30 | 56.5 : 43.5 |
| 12 | 104 | 32.8 | 140–145 | 5 | *** | 66.3 | 1.44 | 59.0 : 41.0 |
| 13 | 156 | 32.8 | 140–145 | 5 | *** | 69.7 | 1.45 | 59.2 : 40.8 |
| 14 | 208 | 32.8 | 135–140 | 5 | *** | 67.0 | 1.33 | 57.1 : 42.9 |
| 15 | 208 | 32.8 | 135–140 | 20 | *** | 61.0 | 1.49 | 59.8 : 40.2 |

\* 10 % $H_2SO_4$ on alumosilicate
\*\* 20 % $H_2SO_4$ on alumosilicate
\*\*\* 10 % $H_2SO_4$ and 1 % Mo on alumosilicate

EXAMPLES 16 to 24

The catalysts that are used for the examples 16 to 23 are prepared as follows:

a. 5% sulfuric acid on $Al_2O_3$ 1600 parts of $Al_2O_3$ having 9 m²/g BET (cf. table 6 : carriers) are impregnated with a solution of 86 parts of 98% sulfuric acid and 740 parts of water, then dried under normal pressure at 105° C.

b. 10% sulfuric acid on $Al_2O_3$

Analogously, 1600 parts of $Al_2O_3$ as stated in a) are impregnated with a solution of 181 parts of 98% sulfuric acid and 701 parts of water, then dried under normal pressure at 105° C.

c. 15% sulfuric acid on $Al_2O_3$

The catalyst of 15% sulfuric acid on $Al_2O_3$ is prepared analogously by applying a solution of 288 parts of 98% sulfuric acid in 640 ml of water on 1600 parts of $Al_2O_3$ as stated in a) and by drying subsequently.

d. 10% sulfuric acid and 1% Mo on $Al_2O_3$

In the same way, 1600 parts of $Al_2O_3$ (as stated in a) are impregnated with a solution of 32.7 parts of ammonium heptamolybdate in 683 parts of water, blended with 184 parts of 98% sulfuric acid, then dried under normal pressure at 105° C.

When using the above described catalysts in an amount of 400 ml, under the specified conditions, there are obtained per hour the isomer distributions and yields of mononitrotoluene such as they are shown in table 3. The nitration product (crude) contains, in addition to the p-isomer and o-isomer, about 3 to 4% of m-nitrotoluene.

Table 3

Nitration of toluene in the gaseous phase while using $Al_2O_3$ having 9 m²/g BET as carrier, impregnated with sulfuric acid or with a mixture of sulfuric acid/Mo.

Table 3

| No. | CH₃-C₆H₅ g | 96% HNO₃ g | Temp. °C | Vacuum mm Hg | catalyst | yield calculated on HNO₃ % | Isomer ratio p/o | p : o |
|---|---|---|---|---|---|---|---|---|
| 16 | 156 | 32.8 | 130–140 | 5 | * | 61.1 | 1.84 | 64.8 : 35.2 |
| 17 | 208 | 32.8 | 135–145 | 5 | * | 76.6 | 1.70 | 63.0 : 37.0 |
| 18 | 156 | 32.8 | 125–135 | 5 | ** | 69.2 | 1.71 | 63.1 : 36.9 |
| 19 | 208 | 32.8 | 130–140 | 5 | ** | 73.3 | 1.68 | 62.7 : 37.3 |
| 20 | 208 | 32.8 | 140–150 | 5 | ** | 42.3 | 2.03 | 67.0 : 33.0 |
| 21 | 104 | 32.8 | 130–140 | 20 | *** | 70.4 | 1.63 | 62.0 : 38.0 |
| 22 | 156 | 32.8 | 125–130 | 20 | *** | 61.6 | 1.67 | 62.6 : 37.4 |
| 23 | 208 | 32.8 | 130–140 | 20 | *** | 71.5 | 1.59 | 61.4 : 38.6 |
| 24 | 208 | 32.8 | 135–145 | | **** | 71.3 | 1.80 | 64.3 : 35.7 |

\* 5% $H_2SO_4$ on $Al_2O_3$
\*\* 10% $H_2SO_4$ on $Al_2O_3$
\*\*\* 15% $H_2SO_4$ on $Al_2O_3$
\*\*\*\* 10% $H_2SO_4$ and 1% Mo on $Al_2O_3$

EXAMPLES 25 to 30

The process of Example 1 is followed with the proviso, however, that the catalysts of table 4 are used and are prepared as follows:

a. 10% $Fe_2(SO_4)_3$ on $Al_2O_3$ 769.6 parts of $Fe_2(SO_4)_3$ (23%) are dissolved in 373 parts of water under heat and the carrier of 1600 parts of $Al_2O_3$ having 9 m²/g BET and being impregnated with this solution is then dried at 105° C. under normal pressure.

b. 10% sulfuric acid and 10% $Fe_2(SO_4)_3$ on $Al_2O_3$ 869 parts of $Fe_2(SO_4)_3$ (23%) are dissolved in 600 parts of water and blended with 204 parts of 98% sulfuric acid. The carrier (1600 parts of $Al_2O_3$ having 9 m²/g BET) is impregnated with this solution, then dried at 105° C. under normal pressure.

c. 10% $Al_2(SO_4)_3$ on aluminum oxide 1600 parts of aluminum oxide having 9 m²/g BET are impregnated with the solution of 313 parts of $Al_2(SO_4)_3 \cdot 18 H_2O$ in 546 parts of water, then dried at 105° C. under normal pressure.

d. 10% sulfuric acid and 10% aluminum sulfate on aluminum oxide

The solution of 389.3 parts of aluminum sulfate. 18 $H_2O$ and 181 parts of 98% sulfuric acid in 480 parts of water is applied onto 1600 parts of aluminum oxide having 9 m²/g BET, then dried at 105° C. under normal pressure.

The reaction conditions applied and the isomer ratios achieved as well as the nitro toluene mixture yields obtained are also specified in table 4. The m-nitrotoluene content is about 3 to 4%.

Table 4

Nitration of toluene in the gaseous phase when using aluminum oxide having 9 m²/g BET as carrier which is impregnated with ferric sulfate, a mixture of sulfuric acid/$Fe_2(SO_4)_3$, aluminum sulfate or a mixture of sulfuric acid/aluminum sulfate.

| No. | CH₃-C₆H₅ g | HNO₃ g | Temp. °C | Vacuum mm Hg | catalyst | yield calculated on HNO₃ | Isomer ratio p/o | p : o |
|---|---|---|---|---|---|---|---|---|
| 25 | 208 | 32.8 | 115–120 | 5 | * | 57.0 | 1.61 | 61.7 : 38.3 |
| 26 | 208 | 32.8 | 130–140 | 5 | ** | 66.2 | 1.47 | 59.5 : 40.5 |
| 27 | 156 | 32.8 | 135–140 | 20 | *** | 57.0 | 1.66 | 62.4 : 37.6 |
| 28 | 208 | 32.8 | 130–135 | 20 | *** | 61.6 | 1.63 | 62.0 : 38.0 |
| 29 | 156 | 32.8 | 135–140 | 20 | **** | 77.3 | 1.57 | 61.6 : 38.9 |
| 30 | 208 | 32.8 | 135–140 | 20 | **** | 74.7 | 1.65 | 62.3 : 37.7 |

\* 10% $Fe_2(SO_4)_3$ on $Al_2O_3$
\*\* 10% $H_2SO_4$ and 10% $Fe_2(SO_4)_3$ on $Al_2O_3$
\*\*\* 10% $Al_2(SO_4)_3$ on $Al_2O_3$
\*\*\*\* 10% $H_2SO_4$ and 10% $Al_2(SO_4)_3$ on $Al_2O_3$

EXAMPLES 31 to 36

The process is carried out according to the method described in example 1 while using the catalyst mentioned in examples 28 and 29. Various concentrated nitric acids are used as nitrating agents. Table 5 shows the thus obtained isomer distributions and yields of nitro toluene, calculated on the starting quantity of nitric acid.

Table 5

Nitration of toluene in the gaseous phase with various concentrated nitric acids in the presence of 10% sulfuric acid and 10% aluminum sulfate on aluminum oxide having 9 m$^2$/g BET, as catalyst.

Table 5

| No. | CH$_3$-C$_6$H$_5$ g | HNO$_3$ conc. % | g (100%) | temp. °C | vacuum mm Hg | yield calculated on HNO$_3$ % | isomer ratio p/o | p : o |
|-----|------|------|------|---------|----|------|------|-------------|
| 31  | 208  | 65   | 32.8 | 130–140 | 20 | 77.9 | 1.47 | 59.5 : 40.5 |
| 32  | 156  | 65   | 32.8 | 120–130 | 20 | 62.6 | 1.63 | 62.0 : 38.0 |
| 33  | 208  | 50   | 32.8 | 135–145 | 20 | 65.6 | 1.42 | 58.7 : 41.3 |
| 34  | 156  | 50   | 32.8 | 140–150 | 20 | 63.6 | 1.60 | 61.5 : 38.5 |
| 35  | 208  | 40   | 32.8 | 135–145 | 20 | 69.6 | 1.32 | 56.9 : 43.1 |
| 36  | 156  | 40   | 32.8 | 135–145 | 20 | 53.3 | 1.69 | 62.8 : 37.2 |

Table 6

Synopsis of the carrier materials used for the present invention

Table 6:

| Carrier | composition | presentation | pore volume | total surface |
|---------|-------------|--------------|-------------|---------------|
| SiO$_2$ | abt. 90 % SiO$_2$, abt. 6 % Al$_2$O$_3$, abt. 2 % oxide of: Fe, Ti, Mg and Ca | balls abt. 6 m φ | 800 ml/kg | 120 m$^2$g |
| alumin-silicate | 87 % SiO$_2$, 13 % Al$_2$O$_3$, 0.02% Na$_2$O, 0.05% Fe$_2$O$_3$ | cylindric pellets 3/16 × 3.16 | 340 ml/kg | 95 m$^2$g |
| Al$_2$O$_3$ | 99 % Al$_2$O$_3$, 0.08 % Na$_2$O, 0.025 % Fe$_2$O$_3$, 0.02 % SiO$_2$ | balls 3 – 6 mm φ | 450 ml/kg | 8 m$^2$/g |

What is claimed is:

1. A process for the production of p-nitrotoluene which comprises reacting toluene with nitric acid in the gaseous phase under reduced pressure and at a temperature of about 80° to 180° C. in the presence of an inorganic catalyst which consists essentially of a carrier substance based on SiO$_2$ and/or Al$_2$O$_3$ impregnated with a high boiling inorganic acid and optionally with metal salts of such an acid.

2. A process according to claim 1, wherein the reaction is carried out under a pressure of about 1 to 10 mm Hg, preferably of about 20 to 50 mm Hg.

3. A process according to claim 2, wherein the reaction is carried out at temperatures of from about 100° to 140° C.

4. A process according to claim 1, wherein the carrier substance is impregnated with H$_2$SO$_4$ or H$_3$PO$_4$.

5. A process according to claim 1, wherein the carrier substance is impregnated with H$_2$SO$_4$ and a sulfate with a trivalent metal cation, preferably with Fe$_2$(SO$_4$)$_3$ and/or with Al$_2$(SO$_4$)$_3$.

* * * * *